US009301689B2

(12) United States Patent
Vanderpohl (10) Patent No.: US 9,301,689 B2
(45) Date of Patent: *Apr. 5, 2016

(54) PATIENT MONITORING SYSTEM (71) Applicant: Hill-Rom Services, Inc., Batesville, IN (US)

(72) Inventor: Irvin J. Vanderpohl, Greensburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/562,024

(22) Filed: Dec. 5, 2014

(65) Prior Publication Data

US 2015/0141838 A1     May 21, 2015

Related U.S. Application Data

(63) Continuation of application No. 13/305,884, filed on Nov. 29, 2011, now Pat. No. 8,907,287.

(60) Provisional application No. 61/418,569, filed on Dec. 1, 2010.

(51) Int. Cl.

| G01J 5/02 | (2006.01) |
|---|---|
| A61B 5/00 | (2006.01) |
| A61B 5/11 | (2006.01) |
| A61B 5/113 | (2006.01) |
| A61B 19/00 | (2006.01) |
| A61G 7/00 | (2006.01) |
| A61B 5/01 | (2006.01) |
| A61B 5/08 | (2006.01) |

(Continued)

(52) U.S. Cl.
CPC ................ *A61B 5/0077* (2013.01); *A61B 5/01* (2013.01); *A61B 5/0816* (2013.01); *A61B 5/113* (2013.01); *A61B 5/1115* (2013.01); *A61B 5/1116* (2013.01); *A61B 5/1118* (2013.01); *A61B 5/1126* (2013.01); *A61B 5/165* (2013.01); *A61B 5/6891* (2013.01); *A61B 5/7278* (2013.01); *A61B 19/52* (2013.01); *A61G 7/00* (2013.01); *A61B 2560/0252* (2013.01); *A61B 2562/043* (2013.01); *A61G 2203/42* (2013.01); *G01J 5/02* (2013.01); *G01J 5/20* (2013.01)

(58) Field of Classification Search
CPC ...................................... G01J 5/02; G01J 5/20
See application file for complete search history.

(56) References Cited

U.S. PATENT DOCUMENTS

| 1,388,242 | A | * | 8/1921 | Dodds .............................. | 5/610 |
| 2,592,166 | A | * | 4/1952 | McLean et al. ................... | 5/611 |

(Continued)

FOREIGN PATENT DOCUMENTS

| WO | WO2006011124 A1 * | 2/2006 |
| WO | WO2006117788 A2 * | 11/2006 |

*Primary Examiner* — Christine Sung
(74) *Attorney, Agent, or Firm* — Barnes & Thornburg LLP (57) ABSTRACT

A patient support apparatus includes a monitoring system having a first detector and a controller. The first detector detects electromagnetic radiation from a first field of view of the first detector and providing a signal indicative of characteristics of the electromagnetic radiation. The controller includes a processor coupled to the first detector and a memory device including instructions that, when executed by the processor, cause the processor to processes the signal from the first detector, translate the signal into an array of data, and evaluate the data in the array to determine characteristics of a patient positioned in the first field of view.

15 Claims, 6 Drawing Sheets

(51) Int. Cl.
*A61B 5/16* (2006.01)
*G01J 5/20* (2006.01)

(56) References Cited

U.S. PATENT DOCUMENTS

| | | | |
|---|---|---|---|
| 2,604,639 A * | 7/1952 | Killifer | 5/611 |
| 3,039,118 A * | 6/1962 | Hutt | 5/611 |
| 3,919,727 A * | 11/1975 | Paine | 5/611 |
| 3,972,320 A * | 8/1976 | Kalman | 600/519 |
| 4,057,240 A * | 11/1977 | Damico et al. | 5/611 |
| 4,087,872 A * | 5/1978 | Smirle | 5/611 |
| 4,152,795 A * | 5/1979 | Rodosta et al. | 5/658 |
| 4,196,425 A * | 4/1980 | Williams et al. | 340/573.4 |
| 4,539,560 A * | 9/1985 | Fleck et al. | 340/573.4 |
| 4,633,237 A * | 12/1986 | Tucknott et al. | 340/573.4 |
| 4,814,751 A * | 3/1989 | Hawkins et al. | 340/573.1 |
| 4,837,877 A * | 6/1989 | Hamada et al. | 5/10.2 |
| 4,907,845 A * | 3/1990 | Wood | 340/573.4 |
| 4,947,152 A * | 8/1990 | Hodges | 340/573.4 |
| 4,952,928 A * | 8/1990 | Carroll et al. | 340/10.41 |
| 5,008,654 A * | 4/1991 | Callaway | 340/573.4 |
| 5,095,560 A * | 3/1992 | Volker | 5/11 |
| 5,107,845 A * | 4/1992 | Guern et al. | 600/473 |
| 5,218,344 A * | 6/1993 | Ricketts | 340/573.4 |
| 5,276,432 A * | 1/1994 | Travis | 340/573.4 |
| 5,353,012 A * | 10/1994 | Barham et al. | 340/573.4 |
| 5,365,217 A * | 11/1994 | Toner | 340/539.11 |
| 5,416,695 A * | 5/1995 | Stutman et al. | 600/300 |
| 5,490,298 A * | 2/1996 | Goldsmith et al. | 5/611 |
| 5,495,288 A * | 2/1996 | Broady et al. | 348/155 |
| 5,505,199 A * | 4/1996 | Kim | 600/323 |
| 5,519,380 A * | 5/1996 | Edwards | 340/573.4 |
| 5,583,758 A * | 12/1996 | McIlroy et al. | 705/2 |
| 5,633,627 A * | 5/1997 | Newham | 340/573.4 |
| 5,650,770 A * | 7/1997 | Schlager et al. | 340/573.1 |
| 5,714,931 A * | 2/1998 | Petite et al. | 340/539.17 |
| 5,732,401 A * | 3/1998 | Conway | 705/29 |
| 5,738,102 A * | 4/1998 | Lemelson | 600/483 |
| 5,740,800 A * | 4/1998 | Hendrickson et al. | 600/300 |
| 5,765,139 A * | 6/1998 | Bondy | 705/7.24 |
| 5,780,798 A * | 7/1998 | Hall-Jackson | 200/85 R |
| 5,781,442 A * | 7/1998 | Engleson et al. | 700/214 |
| 5,831,669 A * | 11/1998 | Adrain | 348/143 |
| 5,844,488 A * | 12/1998 | Musick | 340/573.4 |
| 5,877,675 A * | 3/1999 | Rebstock et al. | 340/286.07 |
| 5,941,836 A * | 8/1999 | Friedman | 600/595 |
| 5,946,659 A * | 8/1999 | Lancelot et al. | 705/3 |
| 5,953,704 A * | 9/1999 | McIlroy et al. | 705/2 |
| 6,049,281 A * | 4/2000 | Osterweil | 340/573.4 |
| 6,067,019 A * | 5/2000 | Scott | 340/573.4 |
| 6,078,261 A * | 6/2000 | Davsko | 340/573.4 |
| 6,104,295 A * | 8/2000 | Gaisser et al. | 340/573.4 |
| 6,125,350 A * | 9/2000 | Dirbas | 705/2 |
| 6,154,139 A * | 11/2000 | Heller | 340/573.4 |
| 6,160,478 A * | 12/2000 | Jacobsen et al. | 340/539.12 |
| 6,169,484 B1 * | 1/2001 | Schuchman et al. | 340/573.1 |
| 6,204,767 B1 * | 3/2001 | Sparks | 340/573.1 |
| 6,259,355 B1 * | 7/2001 | Chaco et al. | 340/286.07 |
| 6,402,691 B1 * | 6/2002 | Peddicord et al. | 600/300 |
| 6,433,690 B2 * | 8/2002 | Petelenz et al. | 340/573.1 |
| 6,466,125 B1 * | 10/2002 | Richards et al. | 340/573.4 |
| 6,524,239 B1 * | 2/2003 | Reed et al. | 600/300 |
| 6,583,727 B2 * | 6/2003 | Nunome | 340/665 |
| 6,611,206 B2 * | 8/2003 | Eshelman et al. | 340/573.1 |
| 6,611,783 B2 * | 8/2003 | Kelly et al. | 702/150 |
| 6,624,754 B1 * | 9/2003 | Hoffman et al. | 340/573.1 |
| 6,640,212 B1 * | 10/2003 | Rosse | 705/7.13 |
| 6,674,403 B2 * | 1/2004 | Gray et al. | 342/463 |
| 6,748,250 B1 * | 6/2004 | Berman et al. | 600/310 |
| 6,753,783 B2 * | 6/2004 | Friedman et al. | 340/573.7 |
| 6,788,206 B1 * | 9/2004 | Edwards | 340/573.1 |
| 6,791,460 B2 * | 9/2004 | Dixon et al. | 340/573.1 |
| 6,804,656 B1 * | 10/2004 | Rosenfeld et al. | 705/3 |
| 6,821,258 B2 * | 11/2004 | Reed et al. | 600/595 |
| 6,822,571 B2 * | 11/2004 | Conway | 340/573.1 |
| 6,830,180 B2 * | 12/2004 | Walsh | 235/385 |
| 6,838,992 B2 * | 1/2005 | Tenarvitz | 340/573.1 |
| 6,876,303 B2 * | 4/2005 | Reeder et al. | 340/573.1 |
| 6,897,781 B2 * | 5/2005 | Cooper et al. | 340/573.1 |
| 6,900,732 B2 * | 5/2005 | Richards | 340/573.1 |
| 6,909,367 B1 * | 6/2005 | Wetmore | 340/539.21 |
| 6,915,170 B2 * | 7/2005 | Engleson et al. | 700/2 |
| 6,941,239 B2 * | 9/2005 | Unuma et al. | 702/141 |
| 6,958,706 B2 * | 10/2005 | Chaco et al. | 340/870.11 |
| 6,968,294 B2 * | 11/2005 | Gutta et al. | 702/188 |
| 6,975,230 B1 * | 12/2005 | Brilman | 340/573.1 |
| 6,987,232 B2 * | 1/2006 | Smith et al. | 200/85 R |
| 7,001,334 B2 * | 2/2006 | Reed et al. | 600/300 |
| 7,035,432 B2 * | 4/2006 | Szuba | 382/103 |
| 7,110,569 B2 * | 9/2006 | Brodsky et al. | 382/103 |
| 7,198,320 B2 * | 4/2007 | Rasmussen | 296/170 |
| 7,242,306 B2 * | 7/2007 | Wildman et al. | 340/573.1 |
| 7,369,680 B2 * | 5/2008 | Trajkovic et al. | 382/103 |
| 7,406,731 B2 * | 8/2008 | Menkedick et al. | 5/618 |
| 7,452,336 B2 * | 11/2008 | Thompson | 600/558 |
| 7,502,498 B2 * | 3/2009 | Wen et al. | 382/128 |
| 7,505,620 B2 * | 3/2009 | Braune et al. | 382/152 |
| 7,612,666 B2 * | 11/2009 | Badawy | 340/541 |
| 7,987,069 B2 * | 7/2011 | Rodgers et al. | 702/189 |
| 8,502,683 B2 * | 8/2013 | Yang | 340/573.4 |
| 2001/0044965 A1 * | 11/2001 | Blevins | 5/611 |
| 2002/0023652 A1 * | 2/2002 | Riaziat et al. | 128/897 |
| 2002/0046423 A1 * | 4/2002 | Vilsmeier | 5/11 |
| 2002/0140559 A1 * | 10/2002 | Zhou et al. | 340/573.1 |
| 2002/0165733 A1 * | 11/2002 | Pulkkinen et al. | 705/2 |
| 2003/0013459 A1 * | 1/2003 | Rankin et al. | 455/456 |
| 2003/0028399 A1 * | 2/2003 | Davis et al. | 705/2 |
| 2003/0058111 A1 * | 3/2003 | Lee et al. | 340/573.1 |
| 2003/0069815 A1 * | 4/2003 | Eisenberg et al. | 705/32 |
| 2003/0167187 A1 * | 9/2003 | Bua | 705/2 |
| 2003/0169171 A1 * | 9/2003 | Strubbe et al. | 340/573.1 |
| 2004/0172290 A1 * | 9/2004 | Leven | 705/2 |
| 2004/0193449 A1 * | 9/2004 | Wildman et al. | 705/2 |
| 2004/0210155 A1 * | 10/2004 | Takemura | A61B 5/00 600/534 |
| 2005/0125899 A1 * | 6/2005 | Hanson et al. | 5/613 |
| 2005/0190062 A1 * | 9/2005 | Sullivan et al. | 340/573.1 |
| 2005/0240086 A1 * | 10/2005 | Akay | 600/300 |
| 2005/0242946 A1 * | 11/2005 | Hubbard et al. | 340/539.12 |
| 2005/0283382 A1 * | 12/2005 | Donoghue et al. | 705/2 |
| 2006/0033625 A1 * | 2/2006 | Johnson et al. | 340/573.1 |
| 2006/0050535 A1 * | 3/2006 | Eisenberg | 705/2 |
| 2006/0056655 A1 * | 3/2006 | Wen et al. | 382/103 |
| 2006/0265805 A1 * | 11/2006 | Bellingroth | 5/11 |
| 2007/0033072 A1 * | 2/2007 | Bildirici | 705/3 |
| 2007/0132597 A1 * | 6/2007 | Rodgers | 340/573.1 |
| 2007/0157385 A1 * | 7/2007 | Lemire et al. | 5/600 |
| 2007/0222599 A1 * | 9/2007 | Coveley et al. | 340/572.4 |
| 2008/0101538 A1 * | 5/2008 | Schliermann | 378/95 |
| 2008/0272918 A1 * | 11/2008 | Ingersoll | 340/573.1 |
| 2009/0044334 A1 * | 2/2009 | Parsell et al. | 5/424 |
| 2009/0062696 A1 * | 3/2009 | Nathan et al. | 600/595 |
| 2009/0209846 A1 * | 8/2009 | Bammer | 600/421 |
| 2010/0141578 A1 * | 6/2010 | Horiuchi et al. | 345/158 |
| 2011/0043630 A1 * | 2/2011 | McClure | A61B 5/1116 348/143 |
| 2012/0029879 A1 * | 2/2012 | Sing et al. | 702/189 |
| 2012/0075464 A1 * | 3/2012 | Derenne | A61B 5/0013 348/135 |

* cited by examiner

PATIENT MONITORING SYSTEM

CROSS REFERENCE TO RELATED APPLICATIONS

This application is a continuation of U.S. patent application Ser. No. 13/305,884, filed Nov. 29, 2011, which claims the benefit of U.S. Provisional Patent Application Ser. No. 61/418,569, filed Dec. 1, 2010, both of which are incorporated herein by this reference.

BACKGROUND

The present invention relates generally to systems for monitoring a patient positioned in a patient support apparatus. More specifically, the present invention relates to capturing images of a patient in a patient support apparatus and performing algorithms on the captured images to determine characteristics about the patient.

SUMMARY

In one aspect of the present invention, a patient support apparatus includes a monitoring system and a controller. The monitoring system includes a first detector detecting electromagnetic radiation from a first field of view of the first detector and providing a signal indicative of characteristics of the electromagnetic radiation. The controller includes a processor coupled to the first detector and a memory device including instructions that, when executed by the processor, cause the processor to processes the signal from the first detector, translate the signal into an array of data, and evaluate the data in the array to determine characteristics of a patient positioned in the first field of view.

In some embodiments the first detector includes an infrared detector. In some embodiments the first detector includes detector capable of detecting visible light. The patient support apparatus of any preceding claim, further comprising a second detector coupled to the processor, the second detector comprising an infrared detector detecting infrared radiation from at least a portion of the first field of view, the second detector providing a signal indicative of characteristics of the infrared radiation.

In some embodiments the memory device includes instructions that when executed by the processor cause the processor to monitor the signal from the second detector, translate the signal from the second detector into an array of data, and evaluate the data in the array to determine characteristics of a patient is positioned in the first field of view.

In some embodiments the memory device includes instructions that, when executed by the processor, cause the processor to monitor the signal from the second detector to translate the signal received into a patient temperature.

In some embodiments the translation of the signal into a patient temperature includes calibrating the signal to compensate for the ambient temperature.

In some embodiments the translation of the signal into a patient temperature includes calibrating signal to compensate for heat loss at the patient's skin.

In some embodiments the characteristic of the patient positioned in the first field of view includes a centroid of the patient related data in the field of view and the controller determines whether the centroid is positioned within an acceptable boundary on the patient support apparatus.

In some embodiments the data array from the first detector is used to target a boundary in the first field of view, the boundary in the first field of view being used to determine a target area for the collection of data from the second detector.

In some embodiments the data array from either the first detector or the second detector is a time series of data.

In some embodiments, the memory device includes instructions that, when executed by the processor, cause the processor to evaluate characteristics of the patient at a first time and evaluate characteristics of the patient at a second time.

In some embodiments, the characteristic of the patient at a second time is compared to the characteristic of the patient at the first time to determine if changes in the characteristics of the patient exceed a threshold.

In some embodiments the threshold is related to excessive patient movement.

In some embodiments the patient movement is determined as a mean of the magnitude of movements over a period of time.

In some embodiments the patient movement is determined as a mean of the variation from a common point out a number of time intervals.

In some embodiments the characteristic of the patient at a second time is compared to the characteristic of the patient at a first time to determine a respiration rate of the patient.

In some embodiments the respiration rate is determined by calculating the time interval between peak temperatures at a target location.

In some embodiments the respiration rate is determined by calculating the time interval between minimum temperatures at a target location.

In some embodiments the threshold related to excessive patient movement is a velocity threshold.

In some embodiments the patient movement is used to determine if a patient is conscious.

In some embodiments the patient movement is used to determine if a patient is agitated.

In some embodiments an infrared detector includes an internal reference for calibrating the data received by the infrared detector to account for any ambient temperature.

In some embodiments a patient supported on a support plane that intersects an image plane of a detector.

In some embodiments the controller corrects the data signal from a detector to compensate for variations in the relationship between the support plane and the image plane.

In some embodiments the relationship between a first detector and a second detector is known.

In some embodiments the centroid of the patient boundary determined by the controller is established at a first time and the relationship between the centroid in the patient boundary is maintained at later times.

In some embodiments the centroid of the patient boundary determined by the controller is recalculated if the patient boundary varies in shape beyond an acceptable threshold.

In some embodiments the monitoring system further includes a local alarm.

In some embodiments the monitoring system communicates with a remote station.

In some embodiments the monitoring system includes a user interface.

In some embodiments the patient support apparatus includes an angle sensor.

In some embodiments the patient support apparatus includes an angle sensor that provides a signal to the controller indicative of the relationship between the support plane and the image plane.

Additional features and advantages of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
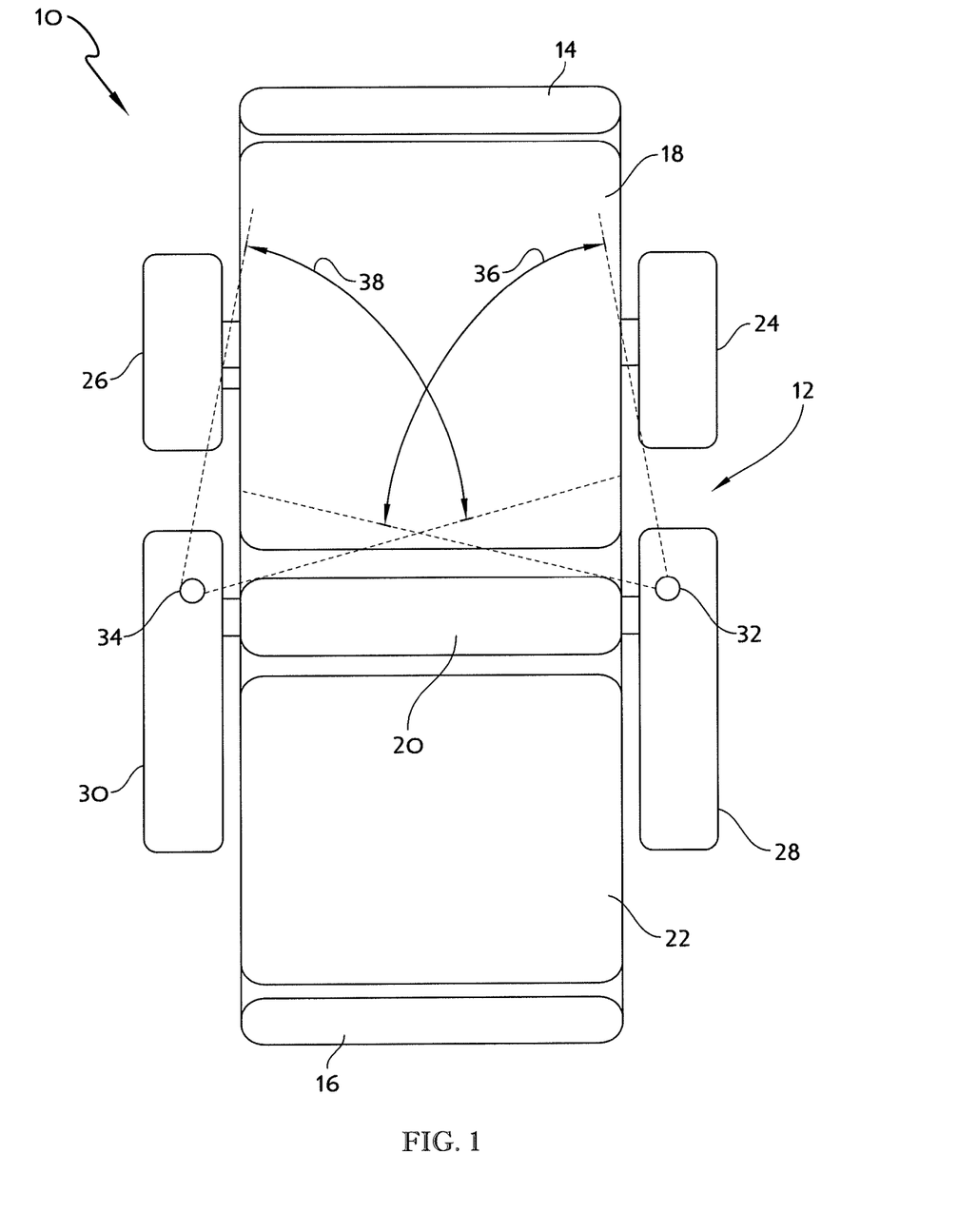
FIG. 1 is a top plan view of a patient support apparatus including detectors mounted to side rails of the patient support apparatus, the detectors positioned to detect characteristics in a field of view that includes the upper body of a patient supported on the patient support apparatus.

A patient support apparatus embodied as a bed 10 includes a patient monitoring system 12. The bed 10 is shown in a top plan view in FIG. 1 and includes a head panel 14, a foot panel 16, a head section 18, a seat section 20, and a foot section 22. The bed 10 also includes a left head side rail 24, a right head side rail 26, a left foot side rail 28 and a right foot side rail 30. The patient monitoring system 12 is shown diagrammatically in FIG. 7 and includes a first detector 32 positioned on the left foot side rail 28 and a second detector 34 positioned on the right foot side rail 30. The first detector 32 has a field of view 36 that includes a significant portion of the head section 18 of the bed 10. The second detector 34 also has a field of view 38 that includes a significant portion of the head section 18. Each of the first and second detectors 32 and 34 detect electromagnetic radiation in their respective fields of view 36 and 38. In some embodiments, the first and second detectors 32 and 34 may be mounted on the left and right head rails 24 and 26 respectively.

In the illustrative embodiment the first detector 32 is a video camera that detects images in the visible light spectrum and the second detector 34 is a video camera that detects images in the infrared light spectrum. In other embodiments, both of the detectors 32, 34 may detect light in the visible light spectrum. In still other embodiments, both of the detectors 32, 34 may detect light in the infrared light spectrum. In use, the first detector 32 detects images from the field of view 36 and converts the images to a data signal that provides information about the image detected. A controller 40 shown in FIG. 7 as part of the monitoring system 12 receives the data signal from the first detector 32 and processes the data signal to evaluate the image from the field of view 36 and make determinations about the image. For example, the controller 40 may be operable to determine if a patient is positioned in the field of view 36 and to determine the position of the patient within the field of view 36.

Figure 2:
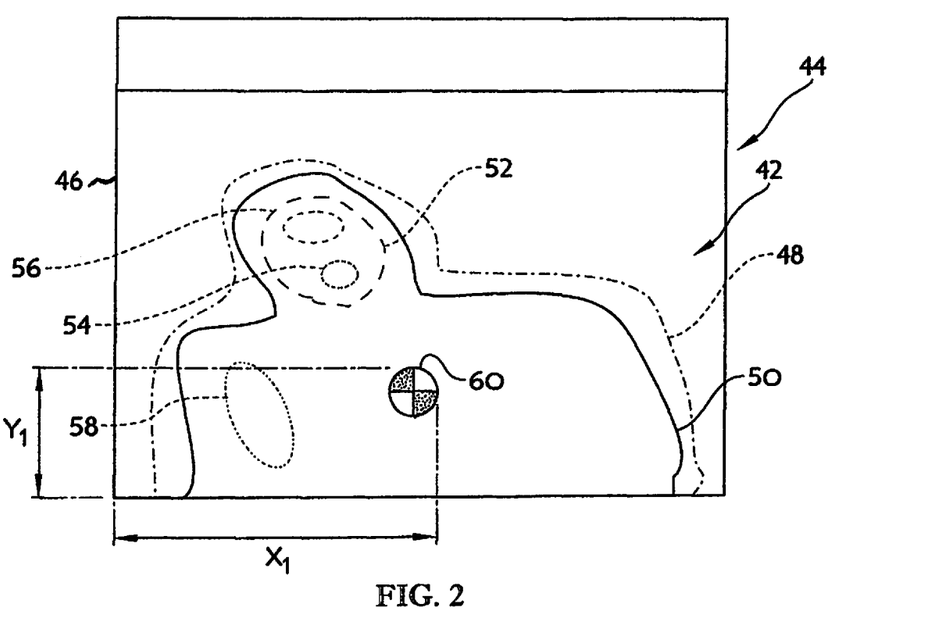
FIG. 2 is a screenshot of an image detected by the detectors of the patient support apparatus of FIG. 1.

Referring now to FIG. 2, a sample image 42 is shown in a display frame 44 on a display device 46 coupled to the controller 40. The image 42 includes several boundary lines that are generated by the controller 40 and corresponding to boundaries used by the controller 40 to distinguish patient characteristics. For example, the boundary 48 has been established by the controller 40 based on the image received by the controller 40 from the first detector 32 and defines the boundary of data that is considered to be related to the presence of a patient in the field of view 36. The determination of the location of the boundary 48 is the result of a mathematical algorithm developed to distinguish the boundary 48. The controller 40 ignores data outside of the boundary 48 as it has been determined to be part of the environment and not in any way related to the patient positioned in the field of view 36.

Figure 3:
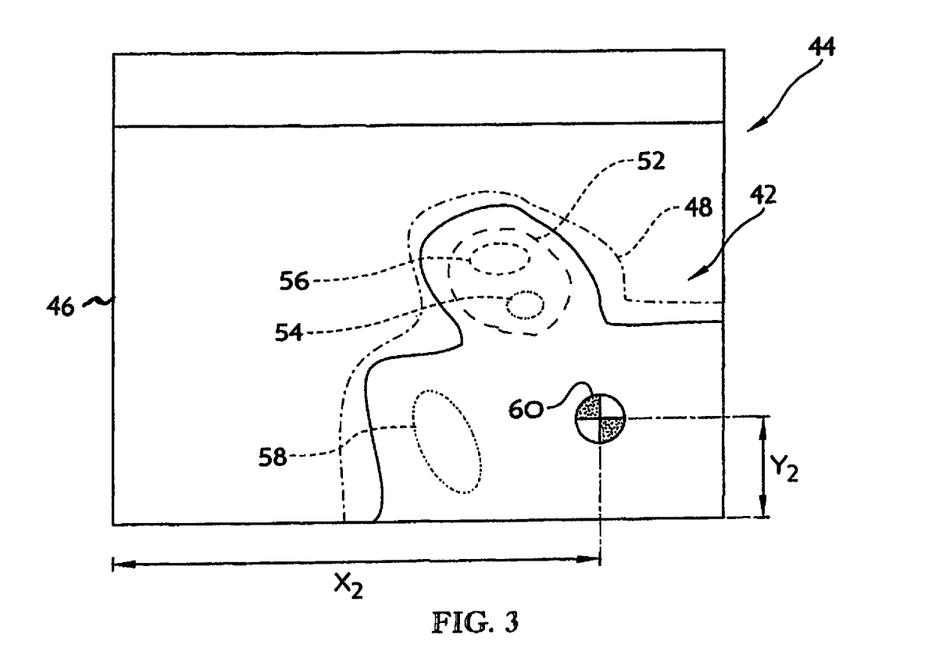
FIG. 3 is a screenshot of another image detected by the detectors of the patient support apparatus of FIG. 1.

Referring again to FIG. 2, the controller 40 establishes a boundary 50 that defines the portion of the image that the controller 40 considers the outline of the patient positioned in the field of view 36. It should be understood that the images shown in FIGS. 2 and 3 represents a single point in time and only the image data related to that particular point in time. The monitoring system 12 may utilize either a single image such as the images shown in the FIGS. 2 and 3 to make certain determinations with respect to the patient positioned in the field of view 36 or the controller 40 may consider more images that have been collected as a time-series array of data to evaluate certain characteristics of the patient. For example, changes in the shape of the boundary 50 over time may indicate patient movement. Also, if an infrared light spectrum detector, such as detector 34, is used, changes in the image may indicate changes in a temperature gradient that may be used to discriminate the data to determine the patient's temperature or the patient's respiration rate. An infrared detector may also operate independently of a visible light detector, with the patient boundary 50 and other boundaries determined by the controller 40 using only data from the infrared detector. Monitoring of the position of the patient, the patient temperature, the patient respiration rate, or other characteristics may be compared to a threshold or allowable value and an alarm may be generated either locally or remotely if the characteristic is not an acceptable value.

Because the first detector 32 and the second detector 34 are positioned with a known relationship, the controller 40 may also simultaneously evaluate the image from the first detector 32 which includes the visible light spectrum and the second detector 34 which includes the infrared light spectrum to make determinations with regard to the status of the patient in the respective fields of view 36, 38. It is within the scope of this disclosure for the image from first detector 32 to be used to assist with targeting of certain areas of the image such that the data from the second detector 34 in the infrared light spectrum may be narrowed to targeted areas to increase the speed at which the images may be processed by ignoring extraneous data. For example, the controller 40 determines that the boundary 52 shown in FIG. 2 generally defines the facial area of a patient in the field of view 36. Based on algorithms, the boundary 54 is identified as the general area in which respiration may be detected by the second detector 34. Thus, by identifying the general location of the boundary 54 for the second detector 34, the image detected by detector 34 may generally be ignored with the exception of the boundary 54 so that a significant amount of the data from the infrared light spectrum does not have to be processed by the controller 40 to determine a respiration rate of the patient.

Figure 4:
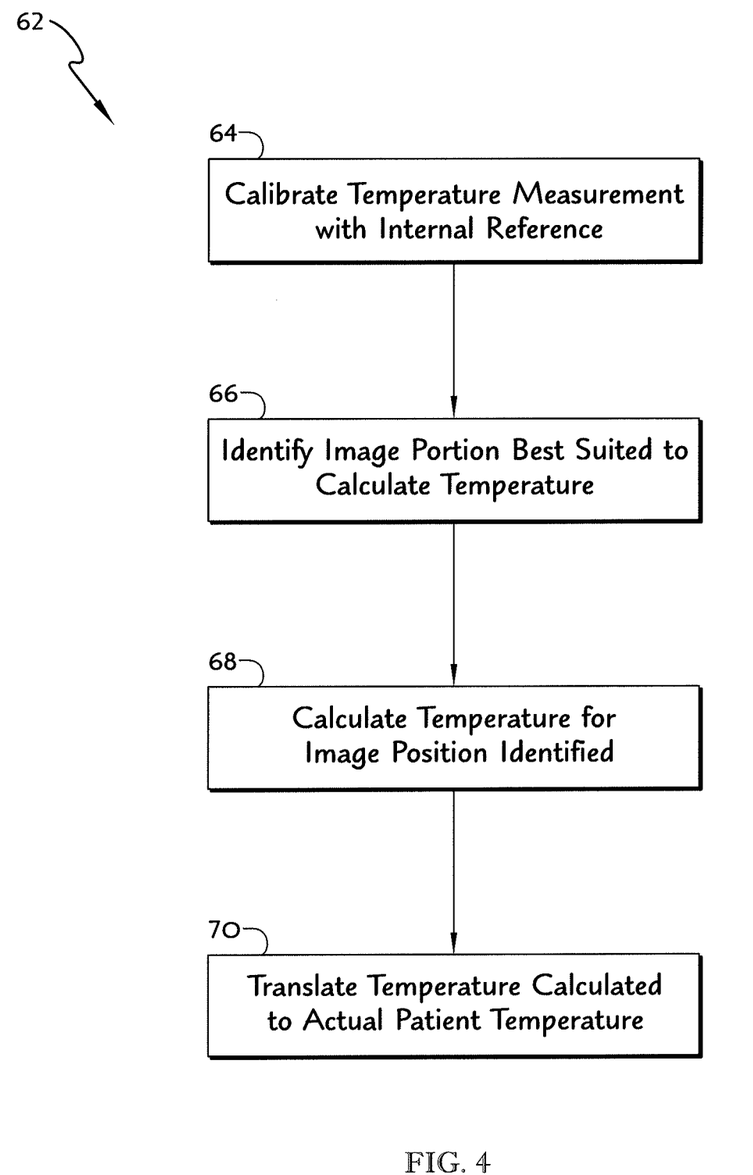
FIG. 4 is a flowchart of a process used to determine the temperature of a patient positioning in the field of view of one of the detectors of the patient support apparatus of FIG. 1.

In addition, a boundary 56 is identified by the controller 40 as a target location for determining the body temperature of the patient. An algorithm used by the controller 40 considers the shape of the patient boundary 50 and the shape of the boundary 52 to determine a general area represented by boundary 56 which includes exposed skin of the patient. Similar to the approach used with regard to the boundary 54, the information from the first detector 32 is used to target the second detector 34 so that minimal data is considered from the infrared light spectrum, thereby reducing the processing required to make the analysis of the patient temperature. A process 62 used by the controller 40 to determine the patient temperature is shown in FIG. 4 and includes a first process step 64 in which the temperature measurement is calibrated using an internal reference. In the illustrative embodiment, the second detector 34 includes an internal thermometer that is used to measure the ambient temperature in the patient room so that the infrared signal detected by the second detector 34 can be offset by a factor that considers the ambient temperature. In some embodiments, the controller 40 may establish a boundary 58 that represents a homogeneous image within the boundary 50. The boundary 58 may then be considered by the controller 40 to be a reference such that the ambient temperature detected by thermometer of the second detector 34 is considered in conjunction with the image data from within boundary 58 to determine a calibration factor for the second detector 34.

The process 62 advances to step 66 where the boundary 56 is determined from the evaluation of boundary 50 and boundary 52 to determine the image portion that is best suited to detect the patient temperature. Once the boundary 56 is developed by the controller 40, the data signal received by the second detector 34 from the boundary 56 is processed by the controller 40 to determine a temperature for the boundary 56 at step 68 of process 62. The process 62 then advances to step 70 where the temperature determined at step 68 is compared to the calibration factor determined at step 64 so that the raw image signal received by the second detector 34 can be translated to an actual patient temperature with accuracy. The translation that occurs at step 70 includes a correction of the temperature determined from boundary 56 to adjust for sheets and blankets, the ambient temperature, and the difference in the temperature sensed at a skin surface as compared to the actual body temperature due to heat loss at the skin surface.

A similar approach can be used to determine the respiration rate of the patient by considering the changes in temperature over time in the area about boundary 54. Once the second detector 34 has been calibrated to compensate for ambient temperature, time series analysis of the data received by the second detector 34 associated with boundary 54 is used to detect changes in the temperature at boundary 54. By measuring the time between the peak temperatures or the minimum temperatures the time between respirations can be determined and directly converted to a respiration rate. In other embodiments, temperature gradient data may be used to determine the respiration rate. For example, the first derivative of the temperature signal may be used to determine the respiration rate.

Information from the first and second detectors 32, 34 may also be used to monitor patient movement. For example, the controller 40 may determine a centroid of the boundary 50 as represented by reference numeral 60 in FIGS. 2 and 3. The position of the patient in FIG. 2 is a representation of the analysis of the data at a first time $t_1$. FIG. 3 is a representation at a second time $t_2$. The position of the centroid 60 is represented by the coordinates $x_1, y_1$ in FIG. 2 at $t_1$ and the position of the centroid 60 is represented by the coordinates $x_2, y_2$ in FIG. 3 at $t_2$. It should be understood that the position of the centroid 60 may be determined at each interval of the time series of data so that changes in the position of the centroid 60 as a function of time may be tracked. Thus, the velocity of the movement of the centroid 60 as well as the absolute position of the centroid 60 may be monitored by the controller 40.

Figure 5:
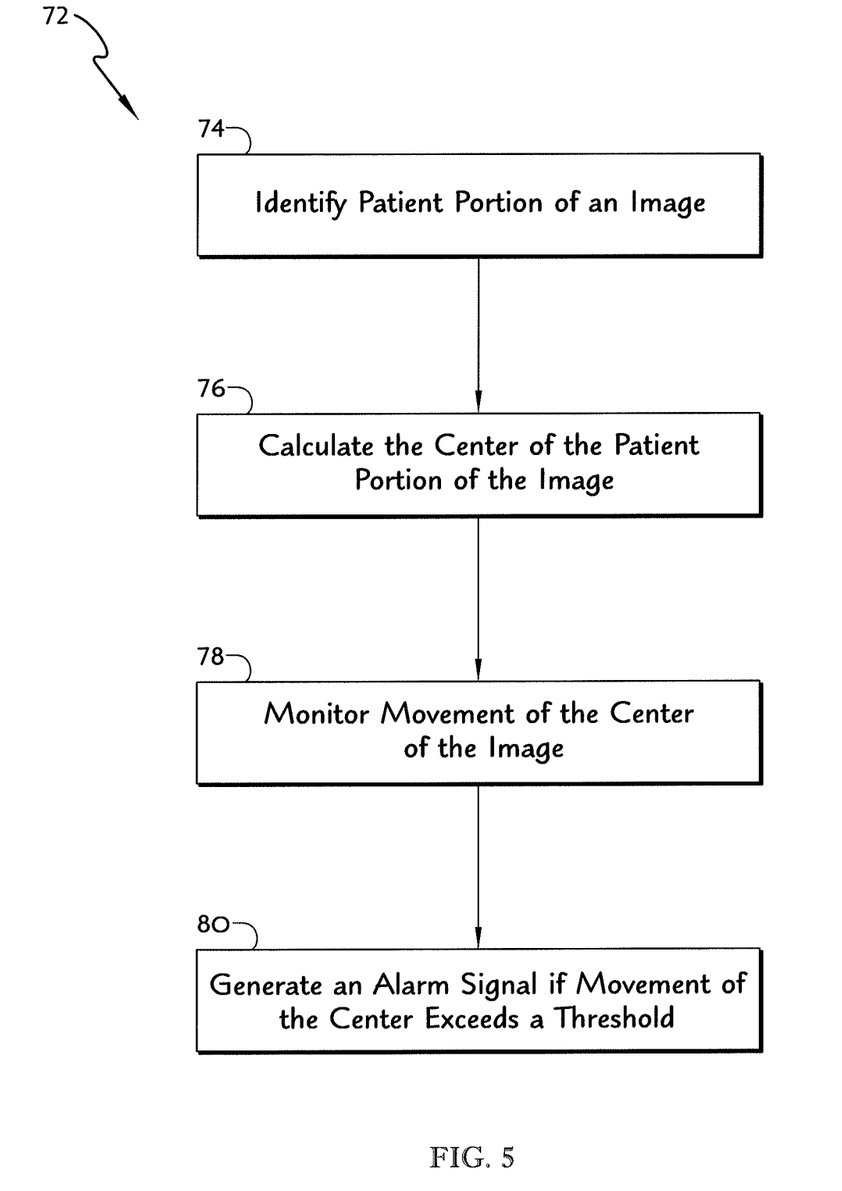
FIG. 5 is a flow chart of a process used to determine characteristics related to the movement of the patient positioned in the field of view of one of the detectors of the patient support apparatus of FIG. 1.

The monitoring of the movement of the centroid 60 provides an indication of patient activity and used to predict that the patient intends to exit the bed, determine that the patient is awake or conscious, or to determine that the patient is stressed or agitated. A process 72 for monitoring patient activity is shown in FIG. 5. At the initial step 74, the patient portion of the image is determined as represented by the boundary 50 in FIGS. 2 and 3. The process 72 then advances to step 76 where the centroid 60 of the patient portion of the image is determined. The process then advances to step 78 wherein the movement of the centroid 60 is monitored over a time series. In the illustrative embodiment shown in FIGS. 2 and 3, the relationship of the centroid 60 to the boundary 50 is held constant such that after the position of the centroid 60 is initially determined, the position of the centroid is anchored to a relationship with the boundary 50 as long as the boundary 50 retains its general shape. Thus, as the patient moves out of the frame 44 detected by the first and second detectors 32, 34 as represented by FIG. 3 and the general shape of the boundary 50 that remains within the frame 44 is consistent with the shape of the boundary 50 shown in FIG. 2. The location of the centroid 60 to that portion of the boundary 50 that remains within the frame 44 is held constant. If however, the patient contorts in some way as to cause the boundary 50 to change shape, the position of the centroid 60 will be recalculated based on the new boundary 50. In either case, the change in the position of the centroid 60 is monitored at step 78 of process 72.

At the step 80 of process 72 an alarm signal is generated if the movement of the centroid 60 exceeds a predetermined threshold. The threshold may be established as a static boundary for the location of the centroid 60 within the frame 44, such that if the centroid 60 moves outside of some limit in either the x-axis or y-axis, an alarm is generated by the controller 40. When the static position alarm approach is used, it may be indicative of a patient who is attempting to egress from the bed 10 or it may be indicative that the patient has moved to an improper position on the bed and needs to be repositioned by a caregiver.

The controller 40 may also monitor the velocity of movement of the centroid 60 to determine if a threshold condition has been met. For example, if the centroid 60 is moving back and forth within the frame 44 at an excessive rate, an alarm may be activated to indicate that the patient is agitated or stressed. Such a condition may also exist if the patient is convulsing. The controller 40 monitors the movement of the centroid 60 within the frame 44 to determine if the velocity or changes in direction exceeded and allowable threshold, thereby indicating that an alarm signal should be generated. It should be understood that the alarm level may be adjustable depending on the expected level of patient activity or the patient risk for fall is the patient is detected to be exiting from the bed 10. In one example, the movement of the centroid 60 may be calculated using a number of samples to determine the mean of the magnitude of movement of the centroid 60 over the sample period as represented by Equation (1) below. In another approach, movement of the centroid 60 may be translated as the mean movement from a starting calibration point over the sample as represented by Equation (2) below.

$$\overline{X} = \frac{\sqrt{(x_1-x_2)^2+(y_1-y_2)^2} + \sqrt{(x_2-x_3)^2+(y_2-y_3)^2} + \sqrt{(x_4-x_3)^2+(y_4-y_3)^2} + \sqrt{(x_5-x_4)^2+(y_5-y_4)^2}}{(4)} \quad \text{EQUATION (1)}$$

$$\overline{X} = \frac{\sqrt{(x_1-x_2)^2+(y_1-y_2)^2} + \sqrt{(x_1-x_3)^2+(y_1-y_3)^2} + \sqrt{(x_1-x_4)^2+(y_1-y_4)^2} + \sqrt{(x_1-x_5)^2+(y_1-y_5)^2}}{(4)} \quad \text{EQUATION (2)}$$

Figure 6:
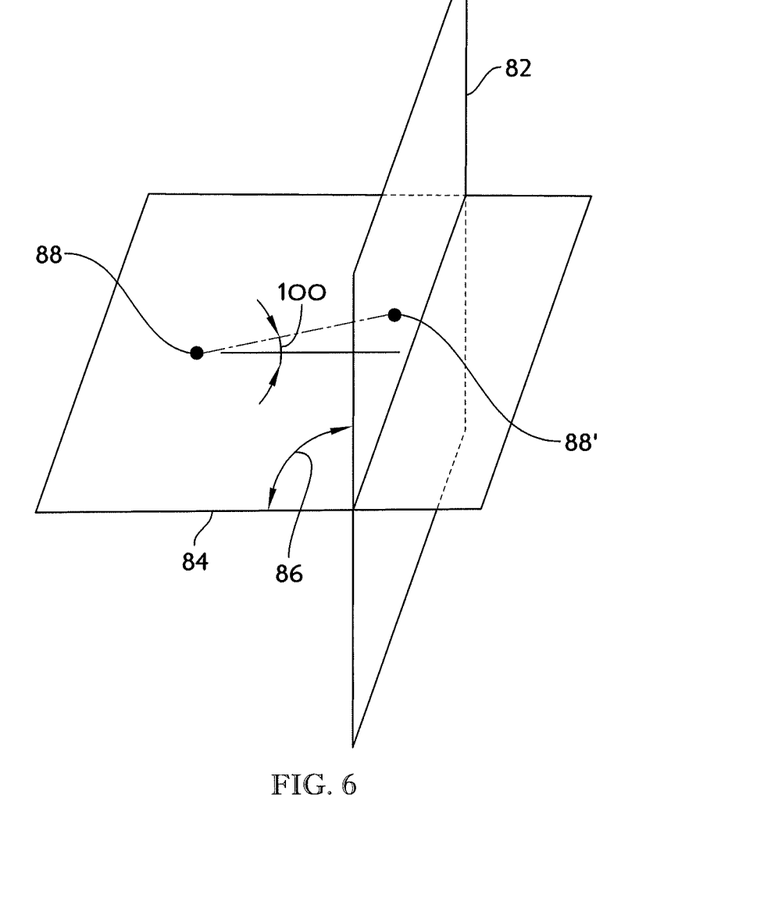
FIG. 6 is a diagrammatic representation of the correction of an image detected by one of the detectors of the patient support apparatus of FIG. 1, the image being corrected to account for the variation in the angular position of a portion of the patient support apparatus of FIG. 1.

The controller 40 may also correct for variations between the image plane and the surface of head section 18 supporting the patient. For example, the support plane 84 shown in FIG. 6 is representative of the support surface of the head section 18 while the image plane 82 is representative of the plane from which the first detector 32 or second detector 34 acquires data. The angle 86 between support plane 84 and image plane 82 is variable as the head section 18 is moved to raise the upper body of the patient as is well known in the art. Because the first detector 32 is mounted on the side rail 28 and the second detector 34 is mounted on the side rail 30, the first detector 32 and second detector 34 do not move as the head section 18 is moved relative to the remainder of the bed 10. The bed 10 includes an angle sensor 90 and the signal from the angle sensor 90 is transmitted to the controller 40 to inform the controller 40 of the angle 86 of the support plane 84 relative to the image plane 82. Reference numeral 88 represents a point on the patient parallel to the support plane 84 and the reference numeral 88' represents the position of the reference 88 on the image plane 82. The angle 100 shown in FIG. 6 represents the deviation of the reference 88 to the reference 88' between the planes 82 and 84. As the angle 86 decreases, the angle 100 increases such that the image detected on the image plane 82 is distorted as the position of the head section 18 changes. The known relationship between the location of the first detector 32 and second detector 34 as compared to the head section 18 and monitoring of the angle sensor 90 allows the controller 40 to compensate for this distortion so that the image detected may be evaluated at any angle 86. This allows the boundary 50 to be determined at any angle 86 so that repositioning of the head section 18 does not cause the loss of position data in the time series.

Figure 7:
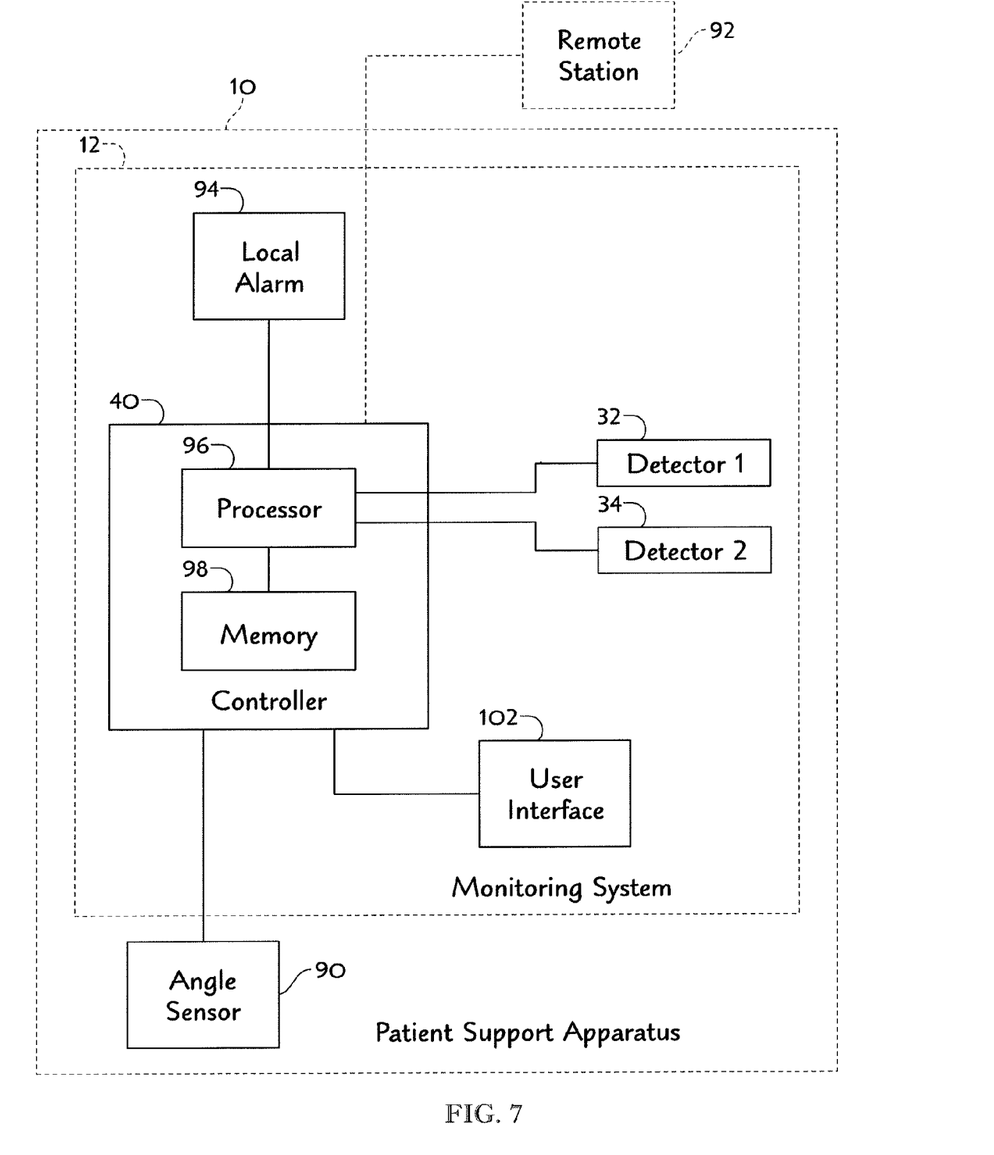
FIG. 7 is a block diagram of the control system for a patient monitoring system according to the present disclosure.

Referring now to FIG. 7, the monitoring system 12 includes the controller 40, the first detector 32, and the second detector 34. The monitoring system 12 also includes a local alarm 94 and a user interface 102 that are each coupled to the controller 40. The user interface 102 includes user inputs that allow information regarding the patient position on the bed to be entered so that the monitoring system 12 may compensate for variations in expected patient movement. A user may also verify certain monitoring parameters during a setup process. For example, the user may enter a patient's temperature so that the monitoring system 12 may use the patient temperature to as part of an algorithm to compensate for the actual patient temperature as compared to the temperature sensed by the monitoring system 12. The controller 40 includes a processor 96 and a memory device 98 coupled to the processor 96. The memory device 98 includes the software accessed by the processor 96 and used by the processor 96 to perform the algorithms discussed herein. The local alarm 94 is coupled to the processor and receives any alarms signals generated by the controller 40 directly from the processor 96. In addition, the monitoring system 12 may communicate alarms to a remote station 92. When present, the remote station 92 is positioned away from the bed 10 at a central location such as a nurse's station, for example.

As described herein, the first detector 32 and second detector 34 may be used to make analysis of the patient image determining a number of patient parameters including the patient body temperature, the respiration rate, the level of patient activity, and the position of the patient on the bed 10. This information may be used to surmise whether a patient is moving out of the bed, conscious, sleeping, or whether or not the patient is in pain. In addition, it should be understood that the approach described herein may also be used to determine whether it is likely that a patient is bleeding, whether the patient has experienced an incontinence event, or if the patient is perspiring excessively. The monitoring system 12 may utilize a single image or a time series of images to make certain evaluations of the patient. In addition to the camera image analysis, detection of patient activity may also incorporate an audio analysis that is considered along with the image analysis to determine if the patient is vocalizing stress, is moaning, or otherwise providing audio indications of issues treated this analysis may include the loudness of any localized stress as well as the duration of any localized stress.

Although the invention has been described with reference to the preferred embodiments, variations and modifications exist within the scope and spirit of the invention as described and defined in the following claims.

The invention claimed is:

1. A patient support apparatus comprising
a monitoring system including a first detector detecting electromagnetic radiation from a first field of view of the first detector and providing a signal indicative of characteristics of the electromagnetic radiation, and
a controller including a processor coupled to the first detector and a memory device including instructions that, when executed by the processor, cause the processor to process the signal from the first detector, translate the signal into an array of data, and evaluate the data in the array to determine a reference point associated with a position of the patient,
wherein the memory device includes instructions that, when executed by the processor, cause the processor to evaluate the reference point associated with a position of the patient at a first time and evaluate the reference point associated with a position of the patient at a second time, wherein the reference point associated with the position of the patient at the second time is compared to the reference point associated with the position of the patient at the first time to determine the movement of the patient,
wherein the controller generates an alarm signal if the movement of the patient exceeds a predetermined threshold, and
wherein the memory device includes further instructions that, when executed by the processor, cause the processor to compare the location of the reference point to a static boundary in the field of view and, if the reference point is positioned outside of the static boundary, activate an alarm.

2. The patient support apparatus of claim 1, wherein the memory device includes further instructions that, when executed by the processor, cause the processor to determine the boundary of a body in the field of view.

3. The patient support apparatus of claim 2, wherein the memory device includes further instructions that, when executed by the processor, cause the processor to monitor the boundary of the body to determine if the boundary changes sufficiently to indicate movement of the body.

4. The patient support apparatus of claim 3, wherein reference point is a centroid of the boundary.

5. The patient support apparatus of claim 4, wherein the patient support apparatus further comprises a second detector detecting electromagnetic radiation from at least a portion of the first field of view, the second detector providing a signal indicative of characteristics of the electromagnetic radiation detected by the second detector.

6. The patient support apparatus of claim 5, wherein the second detector comprises a detector that detects infrared radiation.

7. The patient support apparatus of claim 6, wherein the memory device includes further instructions that, when executed by the processor, cause the processor to utilize the signal from the first detector and the signal from the second detector to determine the boundary.

8. The patient support apparatus of claim 7, wherein the body is supported on a support plane that intersects an image plane of at least one of the first and second detectors, the controller corrects the data signal from at least one of the first and second detectors to compensate for variations in the relationship between the support plane and the image plane, and the patient support apparatus further includes an angle sensor that provides a signal to the controller indicative of the relationship between the support plane and the image plane.

9. The patient support apparatus of claim 7, wherein a data array from the first detector is used to target a boundary in the first field of view, the boundary in the first field of view being used to determine a target area for the collection of data from the second detector.

10. The patient support apparatus of claim 1, wherein the memory device includes further instructions that, when executed by the processor, cause the processor to determine a velocity of the reference point.

11. The patient support apparatus of claim 10, wherein the memory device includes further instructions that, when executed by the processor, cause the processor to determine if the velocity of the reference point exceeds a threshold, and, if the velocity exceeds the threshold, activate an alarm.

12. The patient support apparatus of claim 11, wherein the threshold is variable.

13. The patient support apparatus of claim 12, wherein the patient support apparatus further comprises a second detector detecting electromagnetic radiation from at least a portion of the first field of view, the second detector providing a signal indicative of characteristics of the electromagnetic radiation detected by the second detector.

14. The patient support apparatus of claim 13, wherein the first detector comprises an infrared detector.

15. The patient support apparatus of claim 13, wherein the first detector comprises a detector capable of detecting visible light.

* * * * *